United States Patent [19]

Raudnitz

[11] 4,139,612

[45] Feb. 13, 1979

[54] PROCESS FOR MAKING AN ALUMINUM PHOSPHATE GEL

[75] Inventor: Jean-Paul Raudnitz, Paris, France

[73] Assignee: Laboratoires Biotherax, Plaine Saint-Denis, France

[21] Appl. No.: 775,951

[22] Filed: Mar. 9, 1977

Related U.S. Application Data

[63] Continuation of Ser. No. 393,277, Aug. 31, 1973, abandoned, which is a continuation of Ser. No. 223,785, Feb. 4, 1972, abandoned.

[30] Foreign Application Priority Data

Sep. 23, 1971 [FR] France ............................... 71 34177

[51] Int. Cl.$^2$ ............................................. A61K 33/42
[52] U.S. Cl. .................................................. 424/128
[58] Field of Search .............................. 424/128, 158

[56] References Cited

U.S. PATENT DOCUMENTS

| | | | |
|---|---|---|---|
| 2,294,889 | 9/1942 | Barol | 424/128 |
| 3,591,680 | 7/1971 | Greene et al. | 424/156 |
| 3,692,898 | 9/1972 | Gorman | 424/158 |

OTHER PUBLICATIONS

*Modern Drug Encyclopedia,* Sixth ed. (1955), p. 816.

*Primary Examiner*—Frederick E. Waddell
*Attorney, Agent, or Firm*—Oblon, Fisher, Spivak, McClelland & Maier

[57] ABSTRACT

A medicinal gel is prepared by admixing an anti-gastric mineral gel with an assimilable organic gel in a ratio of from 0.4 to 2.3, together with sweetening and preserving agents.

4 Claims, No Drawings

4,139,612

PROCESS FOR MAKING AN ALUMINUM PHOSPHATE GEL

This is a continuation of application Ser. No. 393,277, filed Aug. 31, 1973, which is a continuation of Ser. No. 223,785, filed Feb. 4, 1972, both abandoned.

BACKGROUND OF THE INVENTION

1. Field Of The Invention:

This invention relates to a stable medicinal gel and more particularly to a mixture of an anti-gastric mineral gel and an assimilable organic gel.

2. Description Of Prior Art:

Aluminum phosphate is well known for its gastric activity and it is known that when aluminum phosphate is applied in the form of a gel, it acts as a veritable dressing for the mucous membranes. Its adhering ability to the stomach walls, however, is not as great as would be desired for many medicinal purposes and ways have been sought for improving its adhesion.

SUMMARY OF THE INVENTION

Accordingly, it is one object of this invention to provide a stable mixed gel which is characterized by a taste that is not disagreeable and which provides greater adhesion to the stomach walls than has heretofore been possible using conventional mineral gels above.

These and other objects as will hereinafter become more readily apparent, have been attained by the admixture of a mineral gel with a colloidal organic gel of vegetable or synthetic origin, which is absorbable without danger by human beings. The mixed gels can be preserved by the use of defined proportions of sugar and preserving agents.

DETAILED DESCRIPTION OF PREFERRED EMBODIMENTS

The mineral gel used herein is a gellified aluminum phosphate.

The organic gel may be any of the conventional gelling agents such as gum gouar, gum tragacanth, gum arabic, gum gleditschia triacanthos, agar-agar, carob flour, pectin (methylated or nonmethylated) carbopol, or methyl cellulose.

The organic gelling agent may be used in a proportion of 0.4 to 2.3 organic gelling agent to mineral gelling agent.

In the usual method of preparing the mixed gel composition, each gel is separately prepared and then mixed and stabilized by the addition of sugar and a preservation agent. Suitable sugars used for this purpose include saccharose, sorbitol, mannitol or combinations thereof. The sweeting agent may further be substituted with minor amounts of artificial sweeting agents such as cyclamate or a derivative thereof, or saccharin or a derivative thereof, which may be added in appropriate quantities to taste.

Suitable preservation agents which are believed harmless to human beings and which are not characterized by a disagreeable taste, include methylparaoxybenzoate, propylparaoxybenzoate, nonylparaoxybenzoate, chlorohexidine, sorbic acid and the sorbates.

It is believed that the addition of the gellifiable organic substance to the mineral gel considerably improves the adherence to the wall of the stomach if it has a structure similar to that of the polysaccharides and that of the mucous present in the secretions of the stomach. This improved adherence is believed not to be solely due to the similarity in structure between the stomach mucous and the organic gel, but also due to the thixotropic properties resulting from the coexistence of the colloidal mineral gel and the organic gel, which is equally colloidal. It is possible to visualize the organic gel as creating a sort of network which holds the mineral gel within its links.

To show the stability of the mixed gel, when an aluminum phosphate gel alone is dispersed in distilled water in an amount of 20%, it was found to settle in 15 minutes. In contradistinction, a mixed gel containing 20% aluminum phosphate and 80% of an organic gel, remained stable for 2-3 hours.

The mixed gel of this invention is suitable for therapeutic applications in the treatment of gastric difficulties, colitis and ulcers. It is believed that its therapeutic activity is due to the combined activity of its chemical properties which enable it to function to neutralize gastric secretions, and to its physical properties, particularly its thixotropic properties which enable it to function as a remarkably good absorbent of toxins at the level or surface of the mucous membranes.

Having generally described the invention, a further understanding can be attained by reference to certain specific examples which are provided herein for purposes of illustration only and are not intended to be limiting unless otherwise so specified.

EXAMPLE 1

1. Preparation of Agar-Agar Gel

A sufficient amount of organic gel, necessary to obtain five tons (metric) of final product, was prepared in a double-walled stainless steel reactor. 750 liters of water was brought to a boil and 13 kg. of 500 agar-agar in powder form and 700 kg. sugar were dissolved therein. The mixture was maintained at boiling temperature for 30 minutes with constant agitation carried out by means of a Rayneri turbine.

Into a second reactor, having single walls and a capacity double that of the first, was transferred, through steel passages, a sweetened solution of agar-agar, into which was dissolved 1 kg. of propylparaoxybenzoate and 4.5 kg. of sorbic acid as a preserving agent. Simultaneously in the first, double-walled reactor there was prepared a solution of 25 kg. of demthylated pectin in 700 liters of water mixed with 50 kg. of sugar. Care should be taken not to exceed 65° C. and to maintain this temperature for 15 minutes while continuing agitation with the Rayneri turbine.

The sugar and pectin were anhydrous to assist their solution and to avoid the formation of clots.

The pectin solution was then transferred to the agar-agar solution in the second reactor.

To improve the formation of the gel, 2.5 kg. of calcium sulphate suspended in 1 liter of water was dissolved into the contents of the second reactor which was agitated constantly for 15 minutes by means of a powerful turbine working slowly at a speed of 300 cycles per minute. The mixture was brought to ambient temperature by means of a cooler or refrigerating group, or by circulating cold water.

2 T 250 of a firm gel having a pretty amber color was obtained.

2. Preparation of the final gel mixture

To obtain a ton of final product, 550 kg of an aluminum phosphate gel was kneaded in a third reactor. That reactor was in the form of a simple enclosure and had a capacity of at least 1,000 kg. The contents were kneaded with the aid of a powerful planetary agitator, for 30 minutes at a temperature of 25°–30° C.

The aluminum phosphate included the following preserving agents per 550 kg. of aluminum phosphate:
- 500 grams of methylparaoxybenzoate
- 100 grams of propylparaoxybenzoate
- 300 grams of sorbic acid
- (25 grams of chlorhexidine digluconate or a 20% solution of Hibitane (Trade Mark) ).

450 kg. of a firm gel prepared according to No. 1 above, and 60 ml. of essence of orange diluted to 2 liters with ethyl alcohol at a temperature of 30° C., was added thereto. The mixture was kneaded for not more than 7 minutes and passed through a homogenizer before being charged into plastic measures.

EXAMPLE 2

The preparation of aluminum phosphate gel was carried out in accordance with the process of Example 1.

To 30 grams of this gel was added 70 grams of an organic gel composed of:

| | |
|---|---|
| Agar-agar | 3 grams |
| Gum Gouar | 6 grams |
| Gum Arabic | 10 grams |
| Sugar | 20 grams |
| Essence of Orange | 0.10 grams |
| Water Q.S.P. | 70 grams |

This gel was permanently stable.

EXAMPLE 3

The procedure of Example 1 was followed with:

| | |
|---|---|
| Aluminum phosphate gel | 68 grams |
| Organic gel | 32 grams |

Composition of this gel:

| | |
|---|---|
| Pectin | 5 grams |
| Methylcellulose | 2 grams |
| Sugar | 10 grams |
| Essence of Mint | 0.10 grams |
| Water Q.S.P. | 32 grams |

The stability was practically permanent.

EXAMPLE 4

The procedure of Example 1 was followed with:

| | |
|---|---|
| Aluminum phosphate gel | 55 grams |
| Organic gel | 45 grams |

Composition of this gel:

| | |
|---|---|
| Pectin | 3 grams |
| Agar-agar | 7 grams |
| Sugar | 15 grams |
| Essence of Orange | 0.05 grams |
| Water Q.S.P. | 45 grams |

The stability was permanent.

EXAMPLE 5

The procedure of Example 1 was followed with:

| | |
|---|---|
| Aluminum phosphate gel | 50 grams |
| Organic gel | 50 grams |

Composition of this gel:

| | |
|---|---|
| Carboxymethylcellulose | 5 grams |
| Carbopol | 1 gram |
| Sugar | 10 grams |
| Saccharin | 0.010 grams |
| Essence of Mandarin | 0.10 grams |
| Water Q.S.P. | 50 grams |

The stability was permanent.

EXAMPLE 6

The procedure of Example 1 was followed with:

| | |
|---|---|
| Aluminum phosphate gel | 35 grams |
| Organic gel | 65 grams |

Composition of this gel:

| | |
|---|---|
| Agar-agar | 7 grams |
| Carob | 5 grams |
| Sugar | 20 grams |
| Cyclamate | 0.001 grams |
| Essence of Mint | 0.05 grams |
| Water Q.S.P. | 65 grams |

The stability was permanent.

EXAMPLE 7

The procedure of Example 1 was followed with:

| | |
|---|---|
| Aluminum phosphate gel | 40 grams |
| Organic gel | 60 grams |

Composition of this gel:

| | |
|---|---|
| Demethylated pectin | 7 grams |
| Agar-agar | 3 grams |
| Calcium sulphate | 0.10 grams |
| Sugar | 20 grams |
| Essence of Curacao | 0.20 grams |
| Water Q.S.P. | 60 grams |

The stability was permanent.

Having now fully described the invention, it will be apparent to one of ordinary skill in the art that many changes and modifications can be made thereto without departing from the spirit or scope of the invention.

Accordingly, what is claimed as new and desired to be secured by Letters Patent is:

1. A medicinal gel comprising a mixture of an aluminum phosphate gel and an assimilable organic gel prepared from a gelling agent selected from the group consisting of gum gouar, gum tragacanth, gum arabic, gum gleditshia, agar-agar, carob flour, demethylated pectin, pectin, methyl cellulose and mixtures thereof, the ratio of organic gel/aluminum phosphate gel being from 0.4–2.3, together with sweetening and preserving agents.

2. The gel of claim 1, wherein the aluminum phosphate gel contains as preserving agents methylparaoxybenzoate, propylparaoxybenzoate, sorbic acid, and chlorohexidine digluconate and the organic gel is composed of a mixture of agar-agar, gum gouar, gum arabic, sugar and essence of orange.

3. The gel of claim 1 in which the sweetening agent is selected from the group consisting of saccharose, sorbitol, mannitol, essences and artificial sweetening agents and combinations thereof in amounts suitable for improving the taste.

4. The gel of claim 1 in which the preserving agent is selected from the group consisting of methylparaoxybenzoate, propylparaoxybenzoate, nonylparaoxybenzoate, chlorhexidine, and sorbic acid.

* * * * *